United States Patent [19]

Wangh

[11] Patent Number: 5,480,772
[45] Date of Patent: Jan. 2, 1996

[54] IN VITRO ACTIVATION OF A NUCLEUS

[75] Inventor: Lawrence J. Wangh, Auburndale, Mass.

[73] Assignee: Brandeis University, Waltham, Mass.

[21] Appl. No.: 13,039

[22] Filed: Feb. 3, 1993

[51] Int. Cl.⁶ .......................... A01N 1/02; A01N 37/18; A61K 37/00; C12Q 1/26
[52] U.S. Cl. .................... 435/2; 514/21; 514/2; 435/23; 435/240.1
[58] Field of Search .................... 435/240.2, 6, 91.1, 435/1, 23, 2, 240.1; 514/1, 2, 21; 424/581

[56]  References Cited

U.S. PATENT DOCUMENTS

| 4,722,598 | 2/1988 | Ford | 530/536 |
|---|---|---|---|
| 4,865,812 | 9/1989 | Kuntz et al. | 422/99 |

OTHER PUBLICATIONS

Jackson, *Seminars in Perinatology* 15:49 (1991).
Bianchi et al., *Proc. Natl. Acad. Sci. USA* 87: 3279 (1990).
Roberts, *Science* 18:378 (1991).
Lohka and Masui, *Science* 220:719 (1983).
Leno and Laskey, *J. Cell Biology* 112:557, (1991).
Gordon et al., *Experimental Cell Research* 157:409 (1985).
Brown et al., *J. Cell Biology* 99:396a (1984).
Wood and Earnshaw, *J. Cell Biology* 111:2839 (1990).
Coppock et al., *Developmental Biology* 131:102 (1989).
Wangh, *J. Cell Science* 93:1 (1989).
Martin et al., in *Preimplantation Genetics*, Plenum Press, New York (Verinsky and Kuliev, eds, 1991).
Murray et al., *Nature* 339:280 (1989).
Young, *Biology of Reproduction* 20:1001 (1979).
Philpott et al., *Cell* 65;569 (1991).
Shamu and Murray, *J. Cell Biology* 117:921 (1992).
Newport and Spann, *Cell* 48:219 (1987).
Henry Harris, in *Cell Fusion* 40–50 (Harvard University Press 1970).
DiBerardino et al., *Proc. Natl. Acad. Sci. USA* 83:8231 (1986).
Orr et al. *Proc. Natl. Acad. Sci. USA* 83:1369 (1986).
Lohka and Masui, *Developmental Biology* 103:434 91984).
Snachez et al., *Journal Of Cell Science* 103:907 (1992).
Coppock et al., Develop. Biol. 131:102–110 (1989) "Replication of Xenopus Erythrocyk nuclei . . . ".

*Primary Examiner*—Margaret Parr
*Assistant Examiner*—Eggerton Campbell
*Attorney, Agent, or Firm*—Lyon & Lyon

[57] ABSTRACT

Products and methods particularly useful for activating and analyzing the nuclei and nucleic acids of human fetal red blood cells or cells found in amniotic fluid thereby facilitating prenatal screening are described. The featured products include activating egg extracts, cytostatic factor (CSF) extracts, kits containing these extracts, and a microchamber microscope slide useful in analyzing nucleus activation.

5 Claims, 3 Drawing Sheets

IN VITRO ACTIVATION OF A NUCLEUS

BACKGROUND OF THE INVENTION

This invention concerns products, methods and apparatus for analysis of human prenatal cells.

Jackson, *Seminars in Perinatology* 15:49 (1991), describes various procedures for prenatal diagnosis, including procedures to diagnose diseases. These procedures involve analysis of the DNA present in early embryonic stages. Specifically, Jackson mentions the use of a polymerase chain reaction to amplify genes, and the possibility of testing oocytes by polar body assay. According to Jackson:

"There are other conceivable embryo biopsy approaches for prenatal diagnosis. The trophectoderm may be obtained at later, multicellular embryonic stages when more cells might be obtained and induced to replicate in tissue culture. . . . Another approach to early prenatal diagnosis is the recovery of fetal cells in the maternal circulation. This tantalizing possibility for a non-invasive method has been pursued for several years by groups in both the United States and the United Kingdom. Both groups originally sought placental immunologic markers for identification and recovery of these cells. Several trophoblast antibodies were developed, some of which appeared to have relative specificity for the fetal cell. After sporadic reports of success, recent articles appear to indicate that these markers are insufficiently specific and actually are attached to maternal cells frequently enough to make this approach unworkable to date."

Bianchi et al., *Proc. Natl. Acad. Sci. U.S.A.* 87: 3279 (1990), describe isolating fetal nucleated erythrocytes in maternal blood using a monoclonal antibody against the transferrin receptor. They state that they "were successful in detecting the Y chromosomal sequence in 75% of male-bearing pregnancies, demonstrating that it is possible to isolate fetal gene sequences from cells in maternal blood."

According to Roberts, *Science* 18:378 (1991), two procedures available for prenatal screening are chorionic villus sampling (CVS) and amniocentesis. Both these procedures have problems involving waiting time and risk of miscarriage, "estimated at 1% to 2% for CVS and 0.5% for amniocentesis." Supra. Roberts also points out a procedure for analyzing nuclear DNA directly when cells are in interphase.

Lohka and Masui, *Science* 220:719 (1983), describe inducing the formation of a nuclear envelope in demembraned sperm of *Xenopus laevis* using a cell-free preparation from the cytoplasm of activated eggs of Rana pipiens.

Leno and Laskey, *J. Cell Biology* 112:557, (1991), performed experiments using erythrocytes from adult chickens. According to Leno:

"Coppock et al. (1989) [Supra] have reported that a pretreatment with trypsin was required for nuclear decondensation and DNA replication of Xenopus erythrocyte nuclei in egg extract. Trypsin pretreatment was not required for nuclear decondensation and DNA replication in our extracts."

Gordon et al., *Experimental Cell Research* 157:409 (1985), describe "a system for the activation of human sperm using cell-free extracts from *Xenopus laevis* eggs." Similarly, an abstract, by Brown et al., *J. Cell Biology* 99:396a (1984), indicate that nuclear changes which occur during the early phases of fertilization can be stimulated by injecting isolated sperm nuclei into heterologous recipient eggs, or by incubating frog sperm nuclei in the presence of cell-free extracts from frog eggs. They state that they found human sperm can be activated in vitro using *Xenopus laevis* frog egg extract to stimulate the early events of nuclear activation, including chromatin decondensation, nuclear enlargement and DNA synthesis.

SUMMARY OF THE INVENTION

This invention features products and methods useful for causing nuclei from human fetal red blood cells or other fetal cells found in amniotic fluid to activate thereby facilitating prenatal diagnosis of various human conditions. Activation of a non-dividing human nucleus leads to nuclear swelling, nucleic acid replication, and nuclear entrance into mitosis thereby producing metaphase chromosomes (arrested metaphase chromosomes or replicating chromosomes). Information about nucleic acid structure and sequences can be obtained by analyzing the nucleic acids present at these different stages.

The featured methods include pretreating a non-dividing human nucleus to enhance its ability to activate, bringing about nuclear activation, and both bringing about and analyzing nuclear activation on a microchamber microscope slide. Other useful methods disclosed include preparing products useful for bringing about activation, such as an activating egg extract and a non-activated cytostatic factor (CSF) extract, an activation assay, and a procedure for cloning whole animals using activated nuclei.

The products including activating egg extract, CSF extract, kits containing these extracts, and a microchamber microscope slide useful in analyzing nuclear activation, are also claimed as part of the present invention.

The nucleus of a fetal erythrocytes is normally small, has condensed chromatin, and does not replicate or divide. Specific nucleic acid sequences in the nucleus of these cells can be stained by fluorescent in situ hybridization methods if the target nucleic acid sequence is accessible to the probe. However, the small size of the nucleus can affect the accessibility of particular nucleic acid sequences and the amount of information obtained from successful hybridization. Moreover, hybridization signals successfully obtained are limited in spacial resolution by the size of the nucleus. As a result, obtaining a reliable fluorescent signal can be difficult and the information obtained by fluorescent staining generally indicates only the presence or absence of accessible specific sequences, and possibly the number of such sequences per nucleus.

In the featured method, the present invention brings about nuclear swelling, DNA replication, and formation of metaphase chromosomes. Genetic information can be obtained from each of these changes in nuclear structure and function. Useful information obtained from these stages of activation include facilitating the visualization of a particular chromosomal region using a probe by increasing the spacial resolution during swelling thereby increasing access of the probe to the chromosomal region; detecting the number of a particular type of chromosome initially present by determining the increased number of the particular chromosome brought about by replication; and visualizing chromosomal morphology by staining metaphase chromosomes, including the presence of one or more sequences at specific locations within chromosomes.

Thus, in the first aspect, the invention features a method for causing a nucleus from a human fetal red blood cell or a fetal cell found in amniotic fluid to activate, thereby bringing about swelling, DNA replication and the formation of metaphase chromosomes. Activation is brought about by contacting a pretreated or, preferably, a further pretreated nucleus, with activating egg extract.

Human fetal red blood cells may be purified using available procedures. One such procedure is that used by Bianchi et al., *Proc. Natl. Acad. Sci. U.S.A.* 87:3279 (1980) The nuclei of these cells can be isolated and pretreated as described in detail below.

Nuclear isolation and pretreatment is preferably carried out using mild conditions. Mild conditions are those which allows for nuclear isolation and pretreatment while causing the minimal amount of protein and nucleic acid damage. Using mild conditions helps maintain the integrity of the nucleic acid thereby decreasing artifacts during subsequent staining, and prevents premature protease activation thereby allowing subsequent protease treatment to occur under controlled conditions chosen to optimize such treatment.

Preferably, nuclear isolation and pretreatment to release a nucleus from its surrounding cytoskeleton thereby forming a pretreated nucleus is carried out in two steps; (1) membrane permeabilization, and (2) separation or alteration (e.g., denature) of cytoskeletal proteins and nuclear matrix proteins. These steps may be carried out simultaneously or separately. Formation of a pretreated nucleus is preferably carried out under conditions minimizing nucleic acid damage and damage to histones.

Membrane permeabilization, opens up the membrane thereby facilitating subsequent nuclear treatment. Different techniques may be used for membrane permeabilization including hypotonic shock, shearing and detergent. Preferably a non-ionic detergent is used to permeabilize the plasma and nuclear membranes. More preferably, lysolecithin is used as the non-ionic detergent.

Different procedures can be use to separate or denature the cytoskeletal proteins surrounding the nucleus and nuclear matrix proteins within the nucleus. These procedures include the use of a thiol reducing agent to denature nuclear protein, using controlled salt extraction to selectively remove cytoskeletal and nuclear matrix proteins, and using controlled poly-anionic treatment to facilitate separation of negatively charged nucleic acid from the positively charged nuclear proteins. Separation conditions should be chosen to ensure a minimal amount of damage to nucleic acids, histones, and non-cytoskeletal proteins. Preferably, a protease is used under mild conditions to remove cytoskeletal proteins surrounding the nucleus. More preferably, trypsin is used as the protease. In the most preferred embodiment, pretreatment is achieved using trypsin and lysolecithin.

Activating egg extracts are used to bring about nuclear activation. Activating egg extracts contain material, such as precursors, protein(s), or mRNA, which support nuclear activation. An egg can be chemically induced to produce materials which brings about nuclear activation. Eggs can be induced using a calcium ionophore as described below. The induced egg continues in its cell cycle. It appears that when an egg is at the point in the cell cycle just prior to the S-phase, the egg cytoplasm is most active in supporting activation. As the egg proceeds into and past the S-phase, it appears to produce material inhibitory to activation.

Preferably activating egg extracts are prepared from Xenopus eggs. More preferably activating egg extract are prepared from eggs having an elevated activation activity. Activation activity refers to the ability of an activating egg extract to bring about activation. Activation activity can be determined by measuring the extent of newly synthesized nucleic acids, occurring during replication, using labelled nucleic acid precursors.

Xenopus eggs induced for 10 minutes to obtain an activating egg extract contain approximately 59% of the optimal activation activity of Xenopus eggs induced for 25 minutes. At about 25–30 minutes the Xenopus eggs are at highest (optimal), or peak, activation activity. Xenopus eggs induced for 40 minutes appear to have a lower activation activity than a peak activation activity. Thus, the present invention discloses the use of induced eggs having an elevated activation activity of 70% or greater of the peak activation activity.

Most preferably activating egg extract is prepared from a number of eggs (e.g., 1,000 to 10,000), most or all of which have an elevated or peak activation activity. Obtaining a large number of eggs having a peak or elevated activation activity is preferably achieved using hardened eggs which have been synchronously induced. Hardened eggs are prepared by hardening the vitelline envelope surrounding the egg (described in detail below). Hardened eggs are less likely to spontaneously induce than soft non-hardened eggs.

Thus, by using hardened eggs a large number of eggs can be collected and induced at the same time (synchronously induced). A given number of eggs synchronously induced should all be at near the same point in their cell cycle at a given later time. Preferably, a large number of eggs having an elevated activation activity are obtained by inducing the eggs at one time, and preparing the activating egg extract from all the eggs at a second later time. Preferably the activating egg extract is stored frozen. Freezing the extract allows a large amount of extract to be prepared at one time and used at different later times.

Various supplements to activating egg extract have been found to increase the activation activity of the activating egg extract. These supplements include cell cycle regulatory proteins, cell cycle inhibitors, cAMP (preferably, between 0.1 and 1.0 mM, most preferably at 0.3 mM), and phosphodiesterase inhibitors (preferably caffeine, more preferably caffeine at a concentration between 0.1 and 10.0 mM, most preferably caffeine at a concentration of 1 mM).

In another preferred embodiment activation occurs under nuclear non-duplication conditions wherein the nucleus swells, replicates DNA, forms metaphase chromosomes and prepares to divide (i.e., enters mitosis), but segregation of sister chromatids is prevented by inhibiting spindle formation. The inhibition of spindle formation prevents the duplication of the cell nucleus and the resulting separation of metaphase chromosomes.

Thus, under non-duplication conditions metaphase chromosomes are detectable for a longer time period and are provided in a "spread pattern." A "spread pattern" refers the orientation of different chromosomes with respect to each other. Drugs such as nocodazole, colchine, or colcemid can be used to inhibit spindle formation. Preferably nuclear non-duplication conditions is achieved by adding nocodazole to the activating egg extract. More preferably, nocodazole is in an amount which will not inhibit DNA replication (e.g., less than 5 μg/ml).

In other preferred embodiments the pretreated nuclei are further pretreated by contact with a CSF extract, or a purified (a more concentrated form than found in a non-activated CSF extract) kinase or a purified phosphatase inhibitor. The desired purified kinase or phosphatase inhibitor can be obtained by purifying the enzymes from CSF fractions and assaying for activation activity. Further pretreatment with CSF is preferably carried out under conditions not resulting in nucleus activation. Premature activation occurs under non-controlled conditions. Possible disadvantages of premature activation include decreased activation because premature activation is occurring under non-optimized conditions, and difficulties in examining nuclei which were activated at different times.

Nuclei further pretreated with a CSF extract activate to a greater extent upon subsequent contact with activating extract, than nuclei not further pretreated with CSF extract. CSF extracts are prepared from non-induced eggs (i.e., eggs arrested in meiotic metaphase II or activated eggs that have been arrested in mitotic metaphase). These extracts contain factors which aid in nucleus activation, such as CSF and mitosis promoting factor (MPF). MPF may help bring about activation and visualization of chromosome by stimulating chromosome condensation and inhibiting spindle assembly.

A preferred source of CSF extracts is Xenopus eggs. Isolation of CSF extract from Xenopus eggs is facilitated using "hardened eggs" which do not spontaneously induce. Preferably, the CSF extract is stored frozen. Freezing the extract allows a large amount of extract to be prepared at one time and used at different later times.

Preferably, CSF extract is supplemented with $Ca^{2+}$ in an amount which increases subsequent activation compared to extract lacking $Ca^{2+}$ activation. The use of $Ca^{2+}$ to supplement CSF extract is particular advantageous if the CSF extract is frozen before use. The $Ca^{2+}$ may be added before freezing or after thawing.

$Ca^{2+}$ is a cofactor for calmodulin activated protein kinases and may increase subsequent activation by increasing the level of phosphorylated topoisomerase II activity. Topoisomerase II is a scaffold protein which aids in chromosome decondensation and condensation possibly by anchoring chromatin loop domains. Wood and Earnshaw, *J. Cell Biology* 111:2839 (1990). In preferred embodiments the $Ca^{2+}$ concentration is greater than 100 µM; more preferably the $Ca^{2+}$ concentration is between 100 µM and 400 µM;

In another preferred embodiment, nuclei are activated under non-synthesis conditions which inhibit nucleic acid synthesis. As a result, the nucleus swells with or without formation of a nuclear envelope but does not replicate DNA or enter mitosis. The resulting increased spacial resolution brought about by nuclear swelling facilitates the use of nucleic acid probes by making regions of nucleic acid more accessible. Non-synthesis condition may be achieved by the addition of reagents such as aphidicolin (e.g., 50–100 µg/ml), mimosine (e.g., at 0.1–1 mM), dideoxycytidine triphosphate (e.g., 0.1 mM) or dideoxythymidine triphosphate (e.g., 0.1 mM).

In another aspect, a non-dividing human nucleus is further pretreated for subsequent activation by contact with a purified protein kinase or a purified phosphatase inhibitor. The purified protein kinase or a purified phosphatase inhibitor is in a purer form than that found in CSF extract.

In a third aspect, the invention features a method for activating a non-dividing human nucleus by further pretreating a non-dividing human nucleus in CSF extract, prepared from hardened eggs, and then contacting these further pretreated nuclei with an activating egg extract prepared from synchronously induced hardened eggs.

In preferred embodiments the CSF extract is frozen before use and the activating egg extract is frozen before use.

In other preferred embodiments, pretreated nuclei undergo further pretreatment in CSF extract involving a warm-then-cold incubation regime. Both the warm and cold steps increase activation of nuclei upon subsequent contact with activating extract. Preferably, incubation is carried out at about 25° C. for at least 30 minutes followed by incubation at about 4° C. for at least 30 minutes. Less preferred, but still an effective incubation, is a warm regime at about 25° C. for at least 30 minutes.

In other preferred embodiments, thawed CSF extract is supplemented with $Ca^{2+}$, preferably the $Ca^{2+}$ concentration is greater than 100 µM, more preferably the $Ca^{2+}$ concentration is between 100 µM and 400 µM, most preferably, $Ca^{2+}$ is in the form of $CaCl_2$.

In another aspect, methods are described for preparing an activating egg extract, from hardened eggs, which can cause non-dividing human nuclei cells to activate. The activating egg extracts are prepared from hardened eggs which have been synchronously induced such that the activating egg extract is prepared from eggs having an elevated activation activity. Preferably synchronous induction is carried out using eukaryotic cells, more preferably Xenopus, yeast, human, echinoderm, mollusc, or fish, or chicken cells are used; even more preferably Xenopus eggs induced for more than 10 minutes are used; most preferably Xenopus eggs are induced for 25–30 minutes.

In another aspect, activation assays are described. These assay measure the degree of activation. A basic assay comprises isolating a nucleus, pretreating the nucleus, further pretreating the nucleus, contacting the further pretreated nucleus with activating egg extract containing labeled nucleotides, and detecting incorporation of label into replicated DNA. Preferably, a radioactive nucleotide is used to determine activation by measuring the extent of DNA replication. The basic assay can be used to measure the affect of additional reagents by adding the reagent at different stages of the assay and measuring activation activity.

Other assays are performed by altering one of the steps of the basic assay. For instance, to assay for important factors in CSF extract, rather than using whole extracts, fractions of the extract are used. These fractions are obtained using standard purification techniques. Similarly, different activating egg extract fractions can be studied.

In a preferred embodiment, a sperm activation assay, particularly useful to study male fertility, is described. Uses of the sperm activation assay include, handling sperm under different condition thereby obtaining optimal handling condition for subsequent in vitro fertilization, and testing the affect of possibly male contraceptive on activation.

In another aspect, a product for further pretreatment of nuclei is described. The further pretreatment product comprises CSF extract supplemented with $Ca^{2+}$. $Ca^{2+}$ is provided in an amount which increases nuclei activation upon subsequent contact with activating extract.

In preferred embodiments the CSF extract is frozen; preferably, $Ca^{2+}$ in an amount greater than 100 µM is added to CSF-extract before or after freezing; more preferably, $Ca^{2+}$ is in an amount between 100 µM and 400 µM; most preferably, $Ca^{2+}$ is in the form of $CaCl_2$.

In another aspect, a product for causing a non-dividing nucleus to activate is described. The activating product comprises an activating egg(s) extract prepared from an egg having an elevated activation activity.

In a preferred embodiment activating egg extract is prepared from Xenopus eggs synchronously induced for more than 10 minutes; preferably the Xenopus eggs are induced for 25 to 30 minutes.

In other preferred embodiments, the activating egg extract is modified by supplementation with cell cycle regulatory proteins, cell cycle inhibitors, cAMP (preferably, between 0.1 and 1.0 mM, most preferably at 0.3 mM), and phosphodiesterase inhibitors (preferably caffeine, more preferably caffeine at a concentration between 0.1 and 10.0 mM, most preferably caffeine at a concentration of 1 mM)

In a related aspect, a kit is disclosed for activating a non-dividing nucleus. The kit is comprised of frozen activating egg extract prepared from an egg having an elevated activation activity and frozen CSF extract.

In a preferred embodiment the CSF extract contains $Ca^{2+}$. In a most preferred embodiment the kit contains a microchamber microscope slide.

In another aspect, the invention features a microchamber microscope slide provided with an upper surface having a water-repellent material of a known thickness defining a microchamber on the upper surface. The microchamber is shaped to enhance flushing of the microchamber, and connected by at least one channel to a well on the upper surface.

In preferred embodiments, the microchamber is teardrop-shaped or pear-shaped; preferably two wells are provided at opposite ends of the microchamber connected by two separate channels to the microchamber; and the microchamber has a defined volume preferably between 5 and 50 μl, more preferably between 10 and 20 μl when a coverslip is placed over it. Fluid can be introduced into the microchamber by placing fluid in one well and allowing it to flow through the microchamber to the opposite well. The fluid is then removed from the opposite well. Removal may be achieved by pipetting away the fluid or by capillary action by placement of a filter paper within the well.

In other preferred embodiments, the water-repellent material is a tape or a coating on the upper surface of the slide, more preferably a TEFLON® coating, or a wax film (e.g., a PARAFILM®). In most preferred embodiments, the upper slide surface is treated to enhance cell growth compared to an untreated slide, the slide is provided in a sterile condition, and/or the slide is coated with an antibody able to specifically bind to a human fetal red blood cell or amniotic fluid cell.

The advantages of the present invention include, but are not limited to, facilitating prenatal screen by optimizing conditions for nuclear activation, which causes the nucleus of a fetal blood cell to swell, replicate nucleic acid, and form metaphase chromosomes. Important information regarding nucleic acid sequences or chromosome morphology can be readily obtained from these various steps by using DNA probes or visualizing the produced metaphase chromosomes. Because fetal blood cells can be obtained from maternal blood supply, an advantage of the invention is a non-invasive procedure to detect the presence of genetic defects.

Other features and advantages of the invention will be apparent from the following description of the preferred embodiments thereof, and from the claims.

DESCRIPTION OF THE PREFERRED EMBODIMENTS

The drawings will first briefly be described.
Drawings

METHODS AND PRODUCTS

Methods for activating nuclei include those described by Coppock et al., *Developmental Biology* 131:102 (1989); Wangh, *J. Cell Science* 93:1 (1989); Wood and Earnshaw, *J. Cell Biology* 111:2839 (1990); Leno and Laskey, *J. Cell Biology* 112:557 (1991); Young, *Biology of Reproduction* 20:1001 (1979); Philpott et al., *Cell* 65:569 (1991); Shamu and Murray, *J. Cell Biology* 117:921 (1992); Adachi et al., *Cell* 64:137 (1991); Newport and Spann, *Cell* 48:219 (1987); and Henry Harris, in CELL FUSION 40–50 (Harvard University Press 1970).

DiBerardino et al., *Proc. Natl. Acad. Sci. U.S.A.* 83:8231 (1986), and Orr et al. *Proc. Natl. Acad. Sci. U.S.A.* 83:1369 (1986) describe nuclear transplantation experiments to activate Rana pipiens nuclei. DiBerardino was able to obtain tadpoles having a survival rate of up to a month, by transplanting differentiated somatic cells into enucleated eggs.

The present invention discloses methods and products useful in activating a non-dividing human nucleus. These methods and products are especially useful for analyzing a fetal red blood nucleus or a nucleus from fetal cells found in amniotic fluid.

Preparing a nucleus for nuclear activation and bringing about nuclear activation is described in detail below as four different phases: (1) preparation of non-dividing human nuclei, (2) preparation of activating egg extracts from a source such as activated Xenopus eggs, (3) preparation of non-activated CSF extracts from a source such as non-activated Xenopus eggs, and (4) activation of non-dividing human nuclei with an activating egg extract.

Also described in detail below is a microchamber microscope slide which facilitates bringing about nuclei activation and analysis of nucleic acids in such cells; a kit for bringing about nuclear activation; an activation assay; and a procedure for cloning whole organisms from somatic cell nuclei.

In general, the methods described in the present invention are based upon both preparing CSF and activating egg extracts having a higher activation potency than previous techniques and optimizing conditions for the use of these extract. Activation potency refers to the ability of these extracts to help bring about or cause activation.

These extracts used as described, cause activation of a non-dividing human nucleus thereby inducing swelling, DNA replication and the formation of metaphase chromosomes. Nucleic acid content and structure in the swollen nucleus can then be analyzed by standard procedures. The procedures provided herein regarding nuclei activation are generally based upon existing procedures used in other systems. However, several improvements over the existing systems are disclosed. Furthermore, existing procedures have not previously been used on human fetal red blood cells or fetal cells found in the amniotic fluid, nor was it known if they would produce useful results on such cells.

Examples are given to illustrate different aspects and embodiments of the present invention. It is to be understood that various different modifications are possible and are contemplated within the true spirit and scope of the appended claims. There is no intention, therefore, of limitations to the exact process or disclosure herein presented.

In particular, there is shown below the activation of a human fetal red blood cell nucleus using frozen/thawed activating egg extract without further pretreatment, under non-duplicating conditions. The treated nuclei swelled significantly, replicated DNA, and then entered and arrested in the pre-mitotic state. Such nuclei are useful for prenatal diagnosis. Furthermore, the use of further pretreatment, should increase the rate and extent of nuclear swelling, decrease the time it takes for DNA synthesis to occur after activation, increase the rate and extent of DNA synthesis, and improve the efficiency with which metaphase chromosomes are formed.

I. NUCLEI ACTIVATION (1) Preparation of Nuclei

The present invention provides a method to cause non-dividing human nuclei to activate and form metaphase chromosomes. Before being activated non-dividing human nuclei are isolated and pretreated. A preferred source of non-dividing human cells is fetal erythrocytes isolated from a maternal blood supply. Isolating these cells does not require penetration of the womb. Fetal erythrocytes are recovered from the maternal blood supply using techniques such as antibody staining followed by cell sorting. The present invention is also useful for analyzing other types of non-dividing human cell nuclei, including non-dividing keratinocytes (e.g., those isolated from amniotic fluid) and sperm cells.

Non-dividing human cells are isolated under mild conditions designed to prevent activation of extracellular proteases (for instance those of the plasma), intracellular proteases, or nucleases. Inadvertent protease or nuclease activation during nuclear isolation could result in damaging both the genetic material of the cell and the protein structures within or around the nucleic acid. Possible nucleic acid damage includes, nucleic acid degradation, and damage to the structural state (e.g., supercoiling). One advantage of keeping the protein structure intact, is maintaining the cytoskeletal protein so it can be subsequently separated from nucleic acid under mild conditions minimizing damage to histones and non-skeletal proteins.

Preferably, solutions used to isolate cells contain protease inhibitor. Solutions such as HBSS and NIB solutions can be supplemented as follows: 0.1 mg/ml heparin, 0.1 mM TPCK (N-tosyl-L-phenylalanine chloromethyl ketone), 0.1 mM TLCK (Nα-p-Tosyl-L-lysine chloromethyl ketone), 0.05 mM PMSF (phenylmethylsulfonyl fluoride), or 5 µg/ml leupeptin, 31.25 mM $Na_2S_2O_5$.

After cell purification, the cell nucleus is preferably isolated and pretreated under mild conditions. Nuclear pretreatment is preferably comprised of two steps, which may be carried out simultaneously or separately; (1) membrane permeabilization, and (2) separation or alteration (e.g., denature) of cytoskeletal proteins and nuclear matrix proteins. These treatment should be carried out to minimize the damage to histone proteins within the nucleus.

The separation or alteration of certain protein appears to be a necessary step for activation. In Xenopus erythrocytes, for instance, proteolytic digestion of cytoskeletal proteins, such as vimentin, appears to be a necessary step for subsequent nuclear activation. Coppock et al. *Developmental Biology* 131:102 (1989). The pretreatment should prepare the nucleus for subsequent activation rather than cause activation.

Desired conditions for plasma membrane permeabilization include mild detergent treatment, mild protease treatment, mild shearing, and mild hypotonic shock. Mild conditions are those conditions able to permeabilize the plasma membrane while creating the least amount of damage to the nuclear DNA and proteins. Permeabilization can be detected using trypan blue. Trypan blue is dye which cannot enter intact cells. The entrance of trypan blue into a cell indicates permeabilization. Protein degradation due to inadvertent protease activation can be determined using polyacrylamide gel electrophoresis to look for protein degradation products. The intactness of nuclear nucleic acids can be established by using agarose gel electrophoresis to determine the presence of nucleic acid degradation products.

Possible pretreatments for separation or alteration of cytoskeletal proteins and nuclear matrix proteins include the following:

(a) Treatment with one or more thiol reducing agent such as 10 mM dithiothreitol for a limited time, at a controlled temperature and pH, to denature cytoskeletal protein;

(b) Controlled salt extraction, such as by washing in buffers supplemented with increasing amounts of NaCl or KCl in the range of 0.025 to 1.0M, to selectively remove cytoskeletal proteins and proteins bound to DNA;

(c) Controlled poly-anion treatment, such as heparin at 0.01–1.0 mg/ml or Penta sodium tripolyphosphate at 70 mM, in 10 mM Borate buffer at pH 9.0, to selectively remove positively charged cytoskeletal protein;

(d) Degradation of cytoskeletal proteins using a protease.

The extent of protein and DNA damage can be measured as described above. In the most preferred mode nuclear isolation and pretreatment are both accomplished at the same time using a mild concentrations of lysolecithin (e.g., 40 µg/ml) and protease (e.g., 0.3 µg/ml trypsin), such that a minimal amount of damage to non-cytoskeletal proteins, histones, and nucleic acid occurs. The minimum time and temperature required for detergent and protease treatment should be used. In the case of red blood cells this is 5 minutes at 25° C.

Controlled treatment with ion-selective chelating agents may also be performed as an additional pretreatment. Agents such as 1.2 mM mimosine can chelate of $Cu^{2+}$, $Al^{3+}$, and $Fe^{3+}$. These ions stabilize higher order chromatin structure, thus their chelation may aid in chromatin decondensation.

Methods to terminate the detergent and protease pretreatment include adding proteins (such as 0.4% bovine serum albumin) to adsorb detergents (the bovine serum albumin employed at this step should be prepared by dialysis of commercially available BSA fraction V against distilled water to remove soluble salts followed by lyophilization), and adding protease inhibitors (such as soybean trypsin inhibitor) to the reaction. The pretreated nuclei should be subsequently washed using an ice cold solution designed to preserve genomic DNA intactness. NIB buffer can be used for this purpose. NIB is made up of 250 mM sucrose, 25 mM NaCl, 10 mM Pipes, 1.5 mM $MgCl_2$, 0.5 mM spermidine, and 0.15 mM spermine, pH 7.0.

The overall efficacy of mild conditions to obtain a pretreated nucleus can be determined by: a) microscopic examination of nuclei to assess whether nuclei are free of their surrounding cytoskeleton and are free standing or clumped, clumping of nuclei is a strong indication of nuclear damage since many nuclei get trapped in released DNA; and b) the ability of nuclei to respond to activating egg extract, the use of mild conditions increases subsequent activation of individual nuclei and improves the synchrony and homogeneity with which the entire population of nuclei is activated.

(2) Preparation of Activating Egg Extract

Activating egg extracts are used to cause non-dividing nuclei to swell, assemble nuclear envelopes and lamina, replicate their genomes, enter mitosis, and form metaphase chromosomes. Activating egg extracts contain material, such as precursors, protein(s), or mRNA, required to activate non-dividing cells.

Non-activated eggs can be triggered en masse to produce material which brings about activation, by being chemically induced to enter the cell cycle. Eggs can be induced using a calcium ionophore as described below. The induced eggs continue in it cell cycle. It appears that when an egg is at the point in the cell cycle just prior to the S-phase, the egg cytoplasm is most active in supporting activation. As the egg proceeds into and past the S-phase, it appears to produce material inhibitory to nuclear activation (see Table 1).

One of the benefits of the disclosed procedures is obtaining an activating egg extract having a higher activation activity than activating egg extract disclosed in the prior art. The activation activity can be determined by measuring the synthesis of DNA using labelled precursors as described below.

Hardened Xenopus eggs are a good source for preparing an activating egg extract. Hardened Xenopus eggs are stable for several hours. In contrast, "soft" Xenopus eggs must be used rapidly. As soon as soft eggs are dejellied they tend to induce spontaneously and randomly. This is considered disadvantageous because activating egg extracts prepared from a specific time during the cell cycle, just prior to the S-phase, has a higher activating activity than extracts prepared from other phases of the cell cycle. Thus, it is desirable to synchronously induce a large number of eggs which are all at the same point of the cell cycle, so extracts can be prepared later from a large number of eggs all of which have elevated activation activity at the same time.

Freshly ovulated Xenopus eggs can be hardened by stabilizing the eggs vitelline envelope as described by Wangh, J. *Cell Science* 93:1 (1989). Obtaining freshly ovulated eggs from female Xenopus is facilitated by injection of hormones which cause Xenopus to ovulate. Injecting 600 units human chorionic gonadotropin (HCG) into a Xenopus female generally brings about ovulation within 12–15 hours. Injection of pregnant mare serum gonadotropin 24 hours before HCG treatment significantly increases the yield of mature eggs. Furthermore, repeated ovulation of frogs once every 4–8 months improves the yield of eggs by increasing the synchrony of oocyte development in the ovary.

The freshly ovulated eggs within their jelly coat, are flooded with 0.3×NKH (1×NKH is 40 mM NaCl, 2.5 mM KCl, 7.5 mM Hepes, pH 7.4 with NaOH), for 15–20 minutes. During this time the jelly layers swell. The eggs are then dejellied in 3×NKH containing 2% cysteine, pH 7.9, by gentle swirling for about 5 minutes.

The resulting soft eggs can be "hardened" by immediately rinsing them five times in 3×NKH containing 2 mM $MgCl_2$, 1 mM $CaNO_3$, 10 µM $ZnCl_2$ and letting them stand for at least 20 minutes at room temperature. Hardened eggs are sorted to remove damaged and partially induced eggs. Calcium is required for hardening and must be present in the 3×NKH used to wash cysteine-treated eggs. Eggs washed in the absence of $Ca^{2+}$ and subsequently treated with $Ca^{2+}$, and $Ca^{2+}$ treatment of eggs still in the jelly coat, do not result in hardened eggs. Additionally, adding $Ca^{2+}$ before or during dejellying will not result in hardening.

Activating egg extract is preferably obtained from hardened eggs induced en masse. Induction can be carried according to procedures described by Coppock et al., *Developmental Biology* 131:102 (1989). The procedure described by Coppock et al. as modified, in the following manner, was used to obtain "prepared activating egg extract": 5–15 ml of hardened eggs were rinsed using activation buffer (4 mM NaCl, 0.14 mM potassium gluconate, 2 mM Hepes, 2 mM $MgSO_4$, 0.6 mM $Ca(NO_3)_2$, pH 7.8), and placed in 500 ml of activation buffer; the eggs were then induced by adding calcium ionophore A23187 (10 µM in DMSO; Sigma Chemical Co.) to a final concentration of 100 nM and incubating at room temperature; after 10 minutes calcium ionophore treated eggs were rinsed and induced for an additional 15–20 minutes by incubating in 1.5×NKH containing 2 mM $MgCl_2$, and 0.6 mM $CaCl_2$ (Coppock et al., *supra*, stops the induction at 10 minutes); the eggs were then placed on ice in a siliconized or teflon beaker and washed 3–5× in several hundred milliliters of ice cold EB buffer (EB=50 mM potassium gluconate, 250 mM sucrose, 10 mM potassium HEPES, 1.5 mM $MgCl_2$, pH adjusted to 7.5 with potassium hydroxide); eggs were then transferred to a volumetric polyallomer centrifuge tube, mixed with Versilube F-50 oil (General Electric) at 0.2 ml oil/ml eggs, and tight packed by centrifugation at 40× g for 1 minute, at 2°–4° C.; the overlaying oil and aqueous layers were removed and the eggs were crushed by centrifugation 15 minutes at 9,000× g, at 2°–4° C.; the cytoplasmic layer between the yolk pellet and the overlaying lipid layer was collected from the bottom by puncturing the tube with a syringe needle; cytochalasin B was added to a final concentration of 10–50 µg/ml and the cytoplasmic material recentrifuged for 15 minutes at 9,000× g, at 2°–4° C.; the resulting second cytoplasmic supernatant was recovered and either used fresh or frozen for future use.

This procedure for "prepared activating egg extract" involving an increased induction time of 15–20 minutes over that described in Coppock et al. *supra*, was chosen based upon the following two experiments: 1) plasmid DNA injected into non-activated Xenopus eggs does not begin replication until 25–30 minutes after eggs are induced, during this lag period factors required for DNA synthesis are possibly released, altered, or synthesized within the egg; and 2) extracts prepared from eggs induced for only 10 minutes synthesize additional proteins in vitro which first act to increase DNA synthesis in pretreated Xenopus erythrocyte nuclei and then act to inhibit DNA synthesis in these same nuclei.

The second experiment, "induction optimization," is particularly useful in determining the optimal induction time for obtaining activating egg extract having an elevated activation activity. The experimental results for induction optimization used to obtain an activating egg extract with an elevated activation activity from Xenopus, is shown in Table 1. The same experimental design could be used to establish the induction time need to obtain egg extracts having elevated activation activity from species other than Xenopus.

Induction optimization was carried for Xenopus in the following manner. Xenopus erythrocyte nuclei were isolated and pretreated with lysolecithin and trypsin as described in Example 1 (described below). An activating egg extract was prepared from hardened eggs which were induced for 10 minutes as described above. Both the activating egg extract and the pretreated nuclei were kept on ice (about 4° C.). The activating egg extract was supplemented with 250 µg/ml creatine phosphokinase, 10 mM creating phosphate, 10 µCi $P^{32}$-dCTP and combined with pretreated nuclei (about 200 nuclei/µl). Individual aliquots containing activated nuclei were shifted from 4° C. to 25° C. Cycloheximide to a concentration of 100 µg/ml was added to the individual aliquots at different times. The aliquots were then incubated at 25° C. for a total time, including the time at 25° C. before addition of cycloheximide, of 60 minutes. After 60 minutes, $P^{32}$-dCTP incorporation into newly synthesized DNA was determined.

TABLE 1

| Time CHM Added | Cpm Incorporated into DNA |
|---|---|
| No CHM | 1,296 |
| T = 0 | 2,894 |
| T = 5 | 4,208 |
| T = 15 | 4,937 |
| T = 30 | 3,775 |
| T = 45 | 2,314 |

The result of induction optimization for Xenopus activating egg extract is show in Table 1. The highest observed activation activity was 15 minutes after the addition of cycloheximide. Thus, about fifteen minutes appears to be the additional time required for peak activation activity (total induction time of about 25 minutes). A more precise time point for the activation peak may be readily determined by taking additional experimental time points. Elevated activation activity (more activation activity than zero time), was seen after an additional 5, 15, and 30 minutes. The elevated activation activity decreased from 15 to 30 minutes. After 45 minutes the observed activation activity was below that of the elevated activation activity. The decrease in activation activity observed for incubation times longer than 15 minutes is attributed to the synthesis of proteins inhibitory to activation.

Several proteins present in Xenopus egg extracts are involved in DNA replication. One or more of these could be a positive acting protein synthesized during the first 25–30 minutes after activation responsible for the increase in activation activity. Possible positive acting proteins include: cyclin A, RFA single strand binding protein, cdk2 kinase, and RCC1 protein. There are also several proteins whose synthesis after the first 25 minutes could be responsible for the decrease in activation activity. Possible proteins which could decrease activation activity include cdc2 and cyclin B. Given the evolutionary conserved nature of both the positive and negative acting proteins, and their functions, it is likely that eggs from species other than Xenopus also display an optimal time just before the start of S-phase when their cytoplasm is most active in supporting nuclear activation.

According to Table 1, incubating for 10 minutes provided less than 60% of the peak activation activity observed for activating egg extracts prepared from Xenopus. Using the above techniques, the induction time required for obtaining egg extract having an elevated activation activity (more than 70% of the peak activation) can be obtained for activating egg extract prepared from egg sources other than Xenopus.

Activating egg extracts from "hardened" eggs may be used fresh in which case they support more than one cell cycle in vitro. Alternately, these extracts may be frozen and then thawed, in which case they are able to support one or more cell cycles in vitro.

The activating egg extract is preferably stored frozen in liquid nitrogen in 7.5–10% (v/v) glycerol, by standard techniques or by an increased rapid freezing technique. The increased rapid freezing technique freezes the extract faster than merely suspending in liquid nitrogen. Increased rapid freezing can be achieved by spotting extract, made 7.5–10% (v/v) glycerol, as a 20 µl droplet onto a block of aluminum immersed in liquid nitrogen.

Before use, frozen activating egg extracts are thawed rapidly at room temperature, put on ice, and if desired, supplemented to enhance activation activity. One possible supplement is cyclic-AMP. The addition of 0.1 mM to 10 mM cAMP to activating egg extracts increases the activation activity of the activating egg extract, as measured by subsequent DNA replication in pretreated Xenopus erythrocyte nuclei. cAMP can be broken down by phosphodiesterase. Caffeine is an inhibitor of phosphodiesterase and thus enhances the stability of endogenous and added cAMP. Thus, caffeine and phosphodiesterase inhibitors are another possible supplement. The addition of caffeine to activating egg extract increases subsequent DNA replication in activated Xenopus nuclei.

Appropriate egg extracts can be obtained from sources other than Xenopus. Useful guidelines for choosing an appropriate egg source to make either activating egg extract or CSF extract are provided below. These guidelines are not intended to be a list of required characteristics, but rather a list of considerations useful for choosing an egg source.

Useful guidelines for choosing an appropriate egg source for making egg extracts include the following:

1. Egg/embryo with substantial stores of activating cell cycle material are preferred. Such egg/embryos can be identified as those showing a series of rapid cell cycles, i.e., cell divisions approximately once every hour as compared to once every day.
2. Moderate egg size is preferred. Moderate egg size represents a compromise between the cytoplasmic volume per egg and yolk mass per egg. Preferably a large yield of cytoplasm per volumetric measure of eggs is obtained.
3. A species in which female animals shed a large number of eggs is preferred as a means of increasing the amount of egg extract available from an animal, while keeping the cost of caring for the animal at a minimum. However in some instance, such as the activation of mammalian somatic cell nuclei prior to transplantation into their corresponding eggs, it may be desirable to prepare extracts from mammalian eggs despite their small size and relatively small number per female.
4. Females of the chosen species are preferably identifiable by external characteristics.
5. Females preferably breed in a reasonable period of time (at least once per year), and at a reasonable cost.
6. Eggs are preferably shed as single cells (e.g., not in jelly mass), or easily freed of jelly layers and other major external envelopes.
7. Eggs can preferably be stabilized from activating once freed of extracellular coats. (see e.g., Wangh, J. Cell Science 93:1 (1989)).
8. Females preferably produce high quality eggs which are uniform, regular. These features minimize waste and help in development of automated methods to sort good and bad eggs. Some eggs, such as those of echinoderms and mollusks, are transparent and contain a prominent germinal vesicle nucleus which can be used to judge egg quality. Other eggs, such as those of Xenopus, are not transparent, but have two distinct colors which can also be used to judge egg quality.
9. Eggs are preferably chemically inducible in a synchronous manner such that a number of eggs may be induced at the same time and be approximately at the same point in the cycle at a specified later time (preferably at meiotic metaphase state or mitotic metaphase state). In this way, extracts may be obtained from a number of eggs at the same point in the cell cycle by inducing all the eggs at one time and using all the eggs to prepare an extract at a later time.
10. Females can preferably be chemically induced to ovulate thereby making it possible to increase the production of eggs from a given female.

11. Female are preferably not harmed by the egg collection method. Alternately, if egg collection does harm the female those females for which a commercial use of the carcass exists are preferred.
12. Preferably the eggs allow preparation of extracts that induce nuclear swelling, either without or with concomitant DNA replication. Nuclear swelling without replication can be achieved by removal of membrane vesicles required for nuclear envelope assembly, or by addition of inhibitors of DNA synthesis, such as aphidicolin or mimosine. Nuclear swelling with replication can be achieved using activating egg extracts such as those obtained from Xenopus eggs.
13. It is important that eggs used to prepare CSF extracts can be arrested in either the meiotic metaphase state, or in the mitotic metaphase state. Recovery of chromosomes, rather than interphase nuclei, requires cell cycle arrest in metaphase. For some species, extracts in metaphase arrest can be prepared directly from non-activated eggs, such as unfertilized Xenopus eggs, or can be made to cycle into and arrest in meiotic metaphase. Useful reagents for bringing about and causing arrest in meiotic metaphase include cyclin $\triangle 90$ (a non-degradable form of sea urchin cyclin), other cyclin related peptides, small amounts of CSF-extract (prepared from non-activated Xenopus eggs), components found in non-activated Xenopus eggs (such as c-MOS kinase) or Calyculin A used on echinoderm eggs (Tosuji et. al. *Proc. Natl. Acad. Sci.* 89:10613 (1992)).

(3) CSF Extract Treatment of Nuclei

Non-activated CSF extract is used to aid subsequent human nuclear activation without directly causing nuclear swelling or DNA replication. Nuclei in CSF extract appear to condense into chromosome like structures and may become surrounded by a spindle apparatus. Nuclear activation prior to contact with activating egg extract is disadvantageous. Problems with premature activation include less activation than that obtained using activating egg extract, and different nuclei being activated at different times.

The activation potency of CSF extracts may be increased by various supplements. In addition, the incubation conditions of nuclei in CSF extract can be adjusted to improve the ability of such extracts to enhance activation of the nuclei upon subsequent contact with activating egg extract.

The CSF extract is preferably prepared from non-induced eggs arrested at meiotic metaphase. CSF extract prepared from non-induced eggs arrested at meiotic metaphase contains high levels of mitosis promoting factor (MPF) and the cytostatic factor (CSF or c-Mos kinase). MPF has activity controlling nuclear entry into mitosis and initiation of spindle assembly. Thus, CSF and MPF, are factors present in CSF extract likely to aid in subsequent activation of quiescent nuclei by altering cytosketal proteins and nuclear matrix proteins.

One reason for obtaining CSF extract from eggs arrested at meiotic metaphase, is that MPF is inactivated at anaphase. MPF is composed of two catalytic subunits, $p34^{cdc2}$ and cyclin B. At the onset of anaphase, cyclin B is destroyed resulting in the inactivation of MPF. During anaphase the chromosomes move towards the two opposite poles of the spindle apparatus and subsequently decondense.

CSF extracts from non-induced Xenopus eggs are prepared by a method based on the work of Lohka and Masui, *Developmental Biology* 103:434 (1984), as well as that of Murray et al., *Nature* 339:280 (1989). Eggs are obtained from one or more ovulating frogs as described above. Each batch of freshly ovulated eggs, about 500 to 1000 eggs, is hardened as described above. Damaged and activated eggs are removed. The remaining eggs are combined into a large siliconized glass or teflon beaker and washed 4–5 times at room temperature (about 21° C.) in approximately 500 ml EB-buffer containing 5 mM potassium EGTA, pH 7.5, (EB=50 mM potassium gluconate, 250 mM sucrose, 10 mM potassium HEPES, 1.5 mM MgCl$_2$, pH adjusted to 7.5 with potassium hydroxide). The eggs are then transferred to a volumetric polyallomer centrifuge tube, mixed with Versilube F-50 oil (General Electric) at 0.2 ml oil/ml eggs, and are tight packed by centrifugation at 40× g for 1 minute, at room temperature. The overlaying oil and aqueous layers are removed and the eggs are crushed by centrifugation for 15 minutes at 9,000× g, at 2°–4° C. The cytoplasmic layer between the yolk pellet and the overlaying lipid layer is collected from the bottom by puncturing the centrifuge tube with a syringe needle. Cytochalasin B is added to a final concentration of 10–50 µg/ml and potassium EGTA is added to a final concentration of 1 mM. The cytoplasmic material is mixed by gently pipetting or rocking back and forth, the cytoplasmic material is then centrifuged for 15 minutes at 9,000× g, at 2°–4° C. An alternative centrifugation procedure involves preparation of a high speed supernatant by centrifugation at >100,000× g for 2 hrs at 2°–4° C. In either case, the resulting second cytoplasmic supernatant (hereinafter "prepared CSF extract") is recovered and is either used fresh or is made 7.5–10% in glycerol and frozen for future use in the same manner as activating egg extract. Frozen extracts are used by thawing rapidly at room temperature and then placing on ice. Thawed extracts are supplemented with an ATP regenerating system consisting of 10 mM creatine phosphate, and 10 µg/ml creatine phosphokinase.

The histone H1 kinase activity, the structural state of plasmid DNA added to the CSF extract, and the inability of CSF extract to cause nuclear activation, demonstrated that "prepared CSF extract" was arrested in meiotic metaphase. The histone H1 kinase activity of the CSF extract either before or after freezing was high. Upon activation of the extract with 4 mM Ca$^{2+}$, the histone activity decreased. Negatively supercoiled circular plasmid DNA added to the extract relaxed. Lysolecithin-trypsin pretreated Xenopus erythrocyte nuclei added to CSF extract failed to swell or synthesize DNA.

After further pretreatment in CSF extract, the nuclei may be activated by adding 9 volumes of "prepared activating egg extract." DNA replication, measured by incorporation of labelled nucleotides into DNA strands, may be used to determine the extent to which prior treatment in CSF extract enhances nuclear activation in activating extract. Labelled nucleotides useful in measuring nuclear DNA replication include microcurie amounts of $P^{32}$-dCTP for radioactive measurement of newly synthesized DNA, 16–50 µM biotinylated-dUTP or BrdUTP for fluorescent measurement of newly synthesized DNA, and 250 µM BrdUTP for density labelling of newly synthesized DNA.

Several supplements to the CSF extracts, in the proper concentration, increased the activation potency of CSF extracts without resulting in nuclear activation. β-glycerol-PO$_4$ and Ca$^{2+}$ were found to be particularly useful supplements. The addition of β-glycerol-PO$_4$ increased the rate at which negatively supercoiled DNA relaxed in CSF extract and was subsequently assembled into chromatin. A concentration of about 80 mM was found aid in chromatin assembly without activating the nucleus. Beta-glycerol-PO$_4$ is an inhibitor of phosphatase activity and may act by increasing the level of the phosphorylated functionally-active form of topoisomerase II in the CSF extract. Similarly, the addition of 100 µM Ca²⁺ increased both the rate negatively supercoiled DNA relaxed in CSF extract and rate of subsequent assembly into chromatin. Calcium is a cofactor for calcium calmodulin activated protein kinases and may also act by increasing the level of phosphorylated active topoisomerase II activity in the CSF extract. The addition of 100 µM CaCl$_2$ to thawed CSF extract failed to trigger its entry into the cell cycle as judged by continued high levels of histone HI kinase activity. The addition of 100 µM Ca²⁺ also increased both the amount and the rate of DNA synthesis in erythrocyte nuclei after addition of activating egg extract. CSF extract responded to the addition of 4 mM Ca²⁺ by increasing the rate and extent of chromatin assembly over that seen upon addition of 100 µM Ca²⁺. However, the higher concentration of calcium also activated the CSF extract.

The association of factors, whose presence aids in the extent of subsequent activation, with CSF extract was also examined. Apparently, one or more factors in CSF extract which aid in subsequent DNA replication are loosely held by the nuclei in CSF extract and are lost during washing. Xenopus cell nuclei were pretreated with trypsin and lysolecithin, added to CSF extracts to a concentration of 1000–2000 nuclei per µl, and either washed by diluting into excess NIB buffer and centrifuging, or not washed. Subsequent addition of activating egg extract, to a concentration of 100–200 nuclei per µl, resulted in less DNA replication for washed nuclei. For this reason, CSF extracted treated human nuclei are preferably not washed prior to contact with activating egg extract.

Nuclear activation upon contact with activating egg extract can be increased by manipulating the conditions in which nuclei are incubated in CSF extract during further pretreatment. Useful manipulations can be obtained by regulating the incubation period and temperature. The use of a warm-then-cold regime stimulates subsequent nuclei activation. Both warm and cold steps appear to exert positive effects on subsequent nuclei activation. Preferably, the warm-then-cold regime comprises incubation at about 25° C. for 30–60 minutes followed by incubation at 4° C. for 30–60 minutes.

Trypsin and lysolecithin treated Xenopus red blood cell nuclei incubated in frozen/thawed CSF extract using a warm-then-cold regime and contacted with fresh activating egg extract resulted in extensive and synchronous nuclear envelope formation, swelling, and replication upon contact with freshly prepared activating egg extract. While this system is attractive to aid in activation of human nuclei, because of the convenience of using frozen CSF extract, use of this system on Xenopus erythrocyte nuclei revealed several limitations. One limitation is the need to freshly prepare activating egg extract, which is experimentally inconvenient.

Another limitation observed, was that DNA replication after rising abruptly between 20–60 minutes continued at a low rate. The low level of ongoing replication appeared to delay first mitosis until about 220 minutes. When nuclear envelope breakdown and mitosis did occur at 220 minutes, newly synthesized DNA was fragmented, probably because of incomplete replication.

Using CaCl$_2$ in conjunction with frozen CSF overcomes these limitations. The use of CaCl$_2$ permits synchronous nuclear envelope formation, swelling, replication, entry into mitosis (including formation of chromosome-like structures without DNA fragmentation), and renewed DNA synthesis in a second S-phase when both frozen CSF and frozen activating egg extracts are used. Thus, the use of both a warm-then-cold regime and CaCl$_2$ is particularly advantageous when frozen activating egg extracts and frozen CSF extracts are used to cause nucleus activation. Preferably the CSF extract contains 0.1 to 0.4 mM CaCl$_2$ to increase nuclei activation upon subsequent contact with activating egg extract. At this range of Ca²⁺, nuclei treated in CSF extract should not activate until contact with activating extract.

(4) Activation of Nuclei with Activating Egg Extract.

Activating egg extracts are used to activate non-dividing human nuclei thereby bringing about swelling, DNA replication and formation of metaphase chromosomes. However, nuclear activation can be stopped at various points and information about nucleic acid sequence and structure can be obtained by examining the resulting DNA. Under duplication conditions, the nucleus swells, DNA replicates, and the resultant chromosomes divide. Under non-duplication conditions, the nucleus swells, DNA is replicated, but the resultant chromosomes do not divide. Under non-synthesis conditions the nucleus swells, but DNA is not replicated.

The use of nocodazole, or other drugs like colchine, colcemid, and D$_2$O which inhibit microtubule assembly is preferred for preventing separation of mitotic chromosomes. These drugs prevent the formation of mitotic spindles during the cell cycle. As a result, condensed chromosomes accumulate rather then separate to the cells poles and are readily visualized for karyotypic analysis.

However, the addition of 5 µg/ml nocodazole to activating egg extract decreases the rate of DNA replication. Thus, to maintain a high rate of DNA replication it is necessary to either: 1) use nocodazole at a dose less than 5 µg/ml, such as adding nocodazole to CSF extract at 5 µg/ml and diluting the mixture with 9 volumes of activating egg extract; 2) use another drug such as colchine, colcemid or D$_2$O (deuterium oxide) which may be able to block mitotic spindle formation without inhibiting DNA replication; or 3) add the spindle inhibitor later, i.e., after DNA synthesis is complete but before nuclei proceed into mitosis.

To avoid artifacts such as chromosome fragmentation during nuclear activation it is desirable that complete, rather than partial, replication of nuclear genomes be achieved. The following techniques are useful to assess the extent of genome replication achieved during nuclear activation:

1) Coordinate observations of the kinetics of DNA synthesis, the size of the DNA molecules made, the timing of mitosis following DNA synthesis, and the morphological appearance of nuclei. Complete replication is characterized by a early onset and rapid rate of DNA synthesis in all nuclei, an abrupt cessation of DNA synthesis in all nuclei, followed by rapid entry into mitosis, and renewed replication when nuclei exit mitosis. In addition, newly synthesized DNA molecules are very long (greater than 50,000 base pairs), but are transiently cleaved by type II topoisomerase during the period of chromosome condensation and decondensation.

2) The isotope dilution technique can be used to measure the pool size of DNA precursors in the activating egg extract to establish extent of genome replication, on the basis of the radioactive specific activity of the DNA. The isotope dilution technique can be carried out according to Blow and Laskey, *Cell* 47:577 (1986).

3) BrdUTP density labelling of newly replicating DNA followed by isopycnic centrifugation in CsCl and Southern hybridization can be used to determine if one or more rounds of replication is occurring. During the initial round of semi-conservative replication, incorporation of BrUTP leads to formation of a DNA duplex having one heavy (BrUTP containing) strand and one light strand. The subsequent production of a DNA duplex containing two heavy strands indicates more than one round of replication.

4) DNA replication can be visually measured using biotinylated-deoxynucleotide triphosphates (such as biotin-11-dUTP) or bromodeoxy-UTP. These labeled nucleotides can be added to activating egg extracts and are incorporated into DNA during replication. Nuclei containing the labelled DNA can be recovered and placed in a microchamber microscope slide. The labelled DNA is conveniently visualized by staining with Texas Red streptavidin (for biotin samples) or FITC (fluorescein) anti-BrdUTP antibodies. Total DNA can be visualized using a fluorescent intercalating dye (such as propidium iodide or Hoechst stain) or a fluorescently tagged reagent. In some cases it may be desirable to treat nuclei in the microchamber microscope slide with high salt solutions to stretch the DNA across the glass surface before DNA staining. A fluorescent microscope can be employed to establish whether all regions of the nuclear DNA (stained for instance with Hoechst) contain newly synthesized DNA (stained for instance with biotin-Texas Red streptavidin).

II. MICROCHAMBER MICROSCOPE SLIDE

Figure 4:
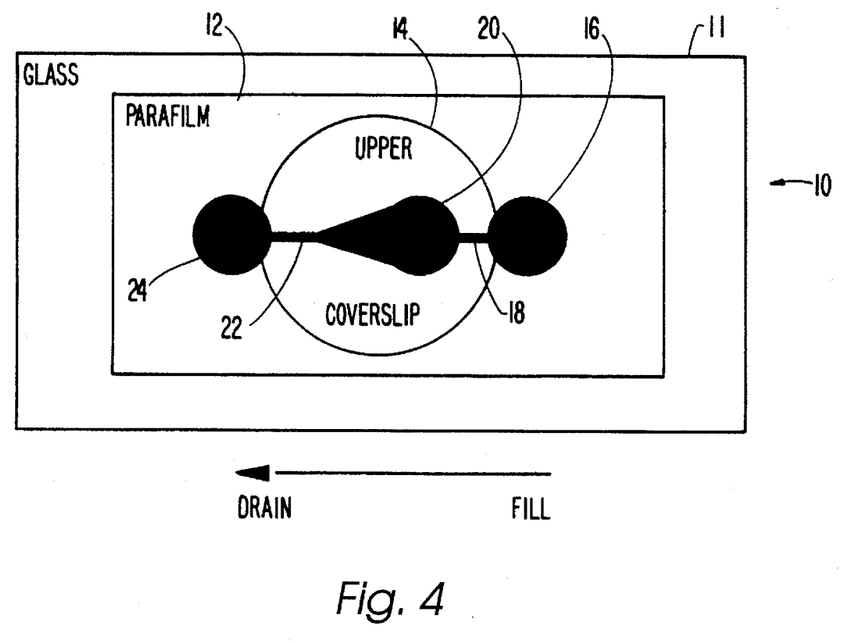
FIG. 4 is a top view of a microchamber microscope slide.

Conversion and analysis of interphase nuclei to meiotic or mitotic chromosomes is facilitated using the microchamber microscope slide. Referring to FIG. 4, there is shown a microchamber microscope slide 10. The microchamber microscope slide allows very small amounts of expensive and hard to come by reagents to be used sequentially on nuclei in situ. For instance, isolated nuclei can be placed into central microchamber 20 which is formed tear-drop shaped, pretreated, swelled, converted to chromosomes, stained, and then read or analyzed without further centrifugation or complex manipulation.

A thin strip of PARAFILM® wax 12, or other appropriate water resistant plastic tape or like material, is annealed to a standard microscope slide 11 or coverslip 14. The microscope slide 11 is generally flat and rectangular-shaped with a top and bottom side. The coverslip 14 is generally flat and circular-shaped with a top and bottom side. The PARAFILM® strip defines three wells connected by two narrow channels. Center microchamber 20 is generally teardrop-shaped with a generally rounded head end and a generally arrow shaped tail end. The volume of the microchamber is preferably between 5 µl and 50 µl, most ideally between 10 µl and 20 µl.

The head end of microchamber 20 is connected to a fill well 16 by a narrow entrance channel 18. The tail end of microchamber 20 is connected to a drain well 24 by a narrow exit channel 22. The volume of the resulting wells is determined by the thickness of PARAFILM® strip 12 and the size and shape of the wells; these parameters are adjustable.

Microchamber 20 is covered by a thin inverted coverslip 14. A thin inverted coverslip is best suited for use with an upright compound microscope. Other types of coverslips may be used. For example, an optically thin coverslip is suited for use with an inverted compound microscope.

In the preferred mode of operation, coverslip 14 completely covers microchamber 20 leaving fill well 16 and drain well 24 substantially uncovered. A sample of cells, nuclei, or other material, is pipetted to the wide part of the microchamber. The microchamber is then covered with a coverslip which is caused to adhere to the upper surface of the PARAFILM® strip 12 by applying two small drops of paraffin oil. The overlaying coverslip can be siliconized to minimize sticking of water and other materials to this surface.

Microchamber 20 is filled by capillary action by placing fluid in fill well 16. Excess fluid is then removed from both the fill well and drain well 24. The microchamber is flushed by placing fluid in the fill well and then sucking the fluid through the microchamber by capillary action achieved by touching blotting paper to the edge of the drain well.

The general teardrop shape enhances flushing of microchamber 20. For a 10 µl microchamber as little as 20 µl of fluid is sufficient to clear the microchamber. If necessary, the coverslip 14 can be removed and the fill channel 18 and exit channel 22 sealed with a small bead of silicone stopcock grease. Material can then be recovered from the microchamber.

The microchamber microscope slide is extremely versatile. It can be sterilized, placed in tissue culture medium, and used as a growing surface for cells. Further, it is possible to increase the depth of the two side wells while leaving the microchamber shallow. Each of the side wells could be covered with their own lid. One of the side wells could be filled several millimeters deep with tissue culture medium while the other well is left unfilled. Tissue culture medium would then flow through the microchamber across the cells until the two side wells reach equilibrium, the exact flow rate being adjustable. Further potential uses include the following: (1) analysis of growing cells; (2) analysis of isolated cells, particularly fetal blood cells; (3) analysis of cell nuclei, or other subcellular particles, organelles or materials; and (4) analysis of material of non-living origin.

The microchamber microscope slide allows analysis of material by essentially all light microscopy staining techniques including the following: (1) fluorescent microscopy of incorporated precursors, antibody staining, nucleic acid hybridization techniques; (2) conventional histological staining procedures; and (3) staining based on enzymatic amplification of molecular signals.

The microchamber microscope slide also allows analysis of biological material by incorporation of radioactive precursors, followed by autoradiographic detection of the incorporated precursors.

The microchamber microscope slide also allows "on-line" microscopic observation of material being treated or altered by fluids flowing through the microchamber. In particular, the microchamber microscope slide is ideally used to both isolate and analyze fetal erythrocytes from maternal blood. Isolation may be achieved by first coating the microchamber with the appropriate antibody to fetal cells, or their already isolated nuclei, and the microchamber is otherwise not sticky. The microchamber itself selects and holds the fetal cells, or nuclei, while the maternal cells, or nuclei, are washed away. The fetal cells, or nuclei, can then be fluorescently tagged in situ and their positions identified even before starting in vitro nuclear swelling and chromosome formation. The fetal cells or nuclei, can then be activated using the appropriate treatments; pretreatment, further pretreatment, and contact with activating egg extract.

III. Activation Kits

The technology disclosed in the present invention can be used to produce activation kits useful for clinical activation of nuclei and scientific research. These kits are particularly useful for prenatal screening. Uses of the activation kit to aid in scientific research include facilitating the study of complex biochemical activities including the assembly of nucleosomes and chromatin on plasmid or viral DNA, formation of eukaryotic nuclear envelopes surrounding nuclear templates, semi-conservative replication of double stranded DNA within eukaryotic nuclei, conservative repair replication of single stranded DNA independent of nuclear envelope assembly, activation of quiescent cell nuclei, nuclear envelope breakdown, condensation of chromatin into chromosomes, formation of meiotic and mitotic spindles, regulated transcription of eukaryotic genes, and protein synthesis.

A basic activation kit comprises frozen activating egg extract and frozen CSF extract. These extracts are prepared based upon the methods described in the present invention. Preferably the kit contains frozen activating egg prepared from eggs having an elevated activation activity. More advanced kits contain various supplements which aid in activation. The various supplements are either in separate containers or are part of the frozen activating egg extract or frozen CSF extract.

Preferably, these supplements are in separate containers. Useful supplements includes $CaCl_2$, nocodazole, $\beta$-glycerol-$PO_4$, phosphodiesterase inhibitor (e.g., caffeine), and cAMP. Preferably, the activation kit contains a microchamber microscope slide.

The activation kits could also be supplemented with reagents used to study activation in general or determine the extent of genome replication. Useful supplements for these activities include radioactive nucleotides, biotinylated nucleotides and different dyes (e.g., biotin-Texas Red streptavidin and Hoechst).

IV. NUCLEI ACTIVATION ASSAY

The procedures disclosed by the present invention, to activate nuclei, can also be used as a general assay procedure to measure nuclei activation. The assay would be particularly useful to identify and purify factors present in CSF extract and to study male fertility.

A basic assay would comprise the steps of isolating a nucleus, pretreating the nucleus, further pretreating the nucleus, contacting the further pretreated nucleus with activating egg extract containing labeled nucleotides, and detecting incorporation of label into replicated DNA. Preferably, a radioactive nucleotide would be used to determine activation by measuring the extent of label incorporated into newly synthesized DNA.

The assay could be tailored to aid in the purification of factors present in CSF which help prepare nuclei for subsequent activation. Specifically, the assay would be performed without the addition of CSF extracts. Rather, various fractions of CSF extract would be obtained by standard purification techniques, and used instead of CSF extract. Those fractions which increase activation activity can then be further purified.

Another use, of a nuclei activation assay, is to study male fertility by measuring the extent of activation of human sperm. In this way, techniques to preserve sperm, to increase in vitro fertilization, and possible male contraceptives, can be tested.

In virtually all species of animals, sperm cells undergo two reaction, capacitation and the acrosome response, before reaching and fusing with the egg surface. After the sperm nucleus enters an egg it undergoes several changes. The nucleus swells, acquires a nuclear envelope and lamina, replicates its DNA, and eventually fuses with the female pronucleus. During this process, sperm basic proteins (histones and protamines), are exchanged for embryonic histones.

It appears that in order for a sperm nucleus to respond to an egg cytoplasm it must first undergo some form of proteolytic digestion. A likely site of necessary proteolytic digestion are non-histone cytoskeletal proteins. Possible contraceptives could target necessary proteolytic enzymes. The affect of the contraceptive could be determined by assaying the degree to which activation is inhibited. Possible contraceptives could also target other enzymes which may be needed for activation.

Alternatively, the assay could be used to determine conditions which result in higher levels of activation thereby finding conditions which enhance fertilization.

Specific uses of the nuclei activation assay include the following:

1) Assaying sperm cell treated under different conditions of preparation, cryopreservation, capacitation and handling;

2) Assaying the affect of sperm cell enzymes (e.g., proteases, nucleases, phosphatases, and kinases), including the inhibition of sperm cell enzymes, on activation;

3) An assay to purify enzymes affecting activation;

4) Assaying the sperm from infertile individuals to determine if infertility is due to problems with sperm nuclear activation;

5) Assaying the ability of specific drugs or reagents to enhance or inhibit activation; and 6) Assaying the affect of inhibitors or activators of sperm cell enzymes on activation;

The specific nuclear activation assay used to study fertility would be tailored to study a particular aspect of activation. For example, to assay the effect of reagents on activation the sperm should be handled and prepared under mild conditions. As discussed above mild conditions are useful in minimizing inadvertent activation of proteases or nucleases. To obtain sperm for the activation assay, fresh sperm samples are first washed in isotonic saline solution under mild conditions. The sperm are then stored by freezing in liquid nitrogen under controlled conditions in the presence of a cryoprotectant. Martin et al., in *PREIMPLANTATION GENETICS*, Plenum Press, New York (Verinsky and Kuliev, eds, 1991).

Fresh or frozen/thawed sperm can be treated under conditions which result in capacitation as described by Martin et al. Supra. The sperm membrane is then permeabilized under mild conditions as described above (e.g., lysolecithin is used to permeabilize the membrane). The nuclei are then recovered from lysed sperm by mild centrifugation in isosmotic buffer. Nuclei are separated from cytoskeletal protein as described above (e.g., using trypsin). The nuclei are then further pretreated (e.g., using CSF extract containing 100 $\mu M$ $Ca^{2+}$). The further pretreated nuclei are contacted with activating egg extract containing a labeled reagent to detect activation (e.g., $P^{32}$-CTP), and activation is measured by determining the extent and the rate of both nuclear swelling and DNA synthesis.

The affect of various reagents can be determined by adding these reagents to the sperm before or after the various individual steps of isolation, pretreatment, further pretreatment or contact with activating egg extract.

V. CLONING WHOLE ANIMALS FROM SOMATIC CELL NUCLEI

The procedures disclosed by the present invention, to activate nuclei, are also useful for preparing a nucleus for subsequent transplantation into an egg for the purpose of directing the development of a new organism. Prior to nuclear transplantation, the nucleus to be transplanted is activated in vitro. The activated nucleus is then transplanted into an egg whose own nucleus has either been removed or functionally inactivated. The egg subsequently develops into an new organism under the direction of genetic information contained in the transplanted nucleus. Uses of cloning somatic cell nuclei include, creation of a clone of genetically identical animals, cloning animals having favorable attributes, and producing more animals which are in danger of becoming extinct.

A difficulty in cloning somatic cell nuclei from mammalian species is that these nuclei are imprinted with patterns of gene structure and function (e.g., DNA methylation patterns) which differ from sperm and egg nuclei patterns. Thus, it is necessary to reprogram somatic cell nuclei before cloning to eliminate the different patterns. Prior activation of somatic cell nuclei in an appropriate egg extract before transplanting should allow for the necessary reprogramming to enable a transplanted nucleus to give rise to either a complete, or substantially complete new organism.

Cloning using a somatic cell nucleus comprises three steps; (1) activating the somatic cell nucleus, (2) preparing a recipient egg, and (3) transplanting the somatic cell nucleus into the egg. The first step is preferably carried out using the improved procedures, disclosed above, to activate a nucleus. Preferably isolation, pretreatment, further pretreatment, and contact with activating egg extract are preformed under conditions where the activated nucleus has a high activation activity.

Preparation of a recipient egg will vary depending upon the egg source. The egg source should be treated in a manner to prevent activation before nuclear transplantation. Procedures to prepare mammalian eggs, such as those described by Martin et al. *supra*, are know in the art.

Preparation of a recipient egg includes destroying the egg's pronucleus. Destruction or removal of the egg's own nucleus guarantees that the eggs genetic material (DNA) does not contribute to the growth and development of the newly cloned individual. One method of destroying the pronucleus is by using ultraviolet light as described by Gurdon, in *METHODS IN CELL BIOLOGY, XENOPUS LAEVIS:PRACTICAL USES IN CELL AND MOLECULAR BIOLOGY*, 36:299–309, Academic Press, California. (Kay and Peng eds., 1991). Alternatively, the egg pronucleus can be surgically removed by procedures known in the art such as those described by King, in *METHODS IN CELL PHYSIOLOGY* 2:1–36, Academic Press, New York (D. M. Prescott, ed., 1966), and McGrath and Solter, *Science* 220:1300–1319 (1983).

Nuclear transplantation can be carried out by standard techniques. These techniques, vary depending upon the species, and are known in the art.

It should be possible to clone Xenopus in the following manner: nuclei from Xenopus red blood cells are isolated, pretreated, and further pretreated. Nuclei are then activated by contact with activating egg extract. The nuclei are activated to different stages in the cell cycle (e.g., S-phase, G2, etc.), and transferred to recipient prepared Xenopus eggs.

Recipient Xenopus eggs are prepared for nuclear transplantation by hardening using $Ca^{2+}$ (as described above), and then irradiating with ultraviolet light to destroy the egg's genome. One to two activated somatic nuclei, in 20 to 50 nanoliters are then microinjected into the Xenopus egg, into the clear cytoplasmic region that lies approximately 400 microns below the animal pole of the egg. The egg is then incubated under conditions that permit cytoplasm rotation. These conditions can be conveniently obtained by floating the egg on Metrizamide®. Rotation of the egg cytoplasm relative to the egg cortex is important for establishment of the proper dorsal/ventral axis of the developing vertebrate embryo.

VI. EXAMPLES

Example 1

CAMP SUPPLEMENT ACTIVATING EGG EXTRACT

The affect of cAMP on DNA replication in activated Xenopus red blood cells was determined. Xenopus nuclei were isolated and pretreated by a method based on Coppock et al., *Developmental Biology* 131:102 (1989), as follows: Xenopus blood was obtained from females by cardiac puncture and collected using a syringe half-filled with Barth's solution (88 mM NaCl, 2.3 mM KCl, 0.82 mM $MgCl_2$ and 10 mM Hepes, pH 7.4) containing heparin (10 mg/ml); the blood was immediately diluted into 10 ml of ice-cold 0.6×SSC (1×SSC is 0.15M NaCl, 0.015M Sodium citrate, pH 7.0) containing 0.1 mg/ml heparin, 0.1 mM TPCK (N-tosyl-L-phenylalanine chloromethyl ketone), 0.1 mM TLCK (Nα-p-Tosyl-L-lysine chloromethyl ketone), 0.05 mM PMSF (phenylmethylsulfonyl fluoride), 5 µg/ml leupeptin, and 31.25 mM $Na_2S_2O_5$; bleeds containing clots, even small ones, were rejected; diluted blood was underlaid with 0.5 volumes of ice cold Metrizamide® (refractive index of 1.3660 in 0.6×SSC) and centrifuged at 180 g for 10 minutes at 4° C., red blood cells pelleted below Metrizamide® while white cells banded above Metrizamide® ; the red cell pellet was resuspended using 0.6×SSC and centrifuged in Metrizamide® four more times to obtain erythrocytes of greater than 99.9% purity; cells were washed three times in NIB and resuspended at $2\times10^8$ cells/ml; cells were then resuspended in NIB:glycerol (7:3) and frozen in aliquots of 100 µl in liquid nitrogen; before using, frozen cells were thawed, diluted to $4\times10^7$ cells/ml in NIB at 23° C., and added to an equal volume of NIB containing 80 µg/ml lysolecithin (40 µg/ml final concentration) and 0.6 µg/ml trypsin (0.3 µg/ml final concentration); after 5 minutes lysolecithin and protease treatment was stopped by adding soybean trypsin inhibitor to a concentration of 10 µg/µl and bovine serum albumin to a final concentration of 0.4%; the resulting nuclei were centrifuged at 800 g at 0° C. for 10 minutes, washed twice in NIB, resuspended with ice-cold NIB and kept on ice.

Isolated and pretreated nuclei were added at 200 nuclei/µl to 550 µl thawed "prepared activating egg extract" supplemented with 5 µg/ml nocodazole, 250 µg/ml cycloheximide, 10 µCi $P^{32}$-dCTP, 10 mM creatine phosphate, and 10 µg/ml creatine phosphokinase. Cyclic-AMP was then added to separate aliquots to yield final concentrations of 0.0 µM, 0.1 µM, 1.0 µM, or 10 µM.

Each aliquot was warmed to 23° C. and sampled over time to determine $P^{32}$-dCTP incorporation into replicated DNA. At each time point, a 7 µl aliquot was taken, frozen on dry ice, and later thawed and digested by the addition of 10 µl replication sample buffer (80 mM Tris (pH 8.0), 8 mM EGTA, 0.13% phosphoric acid, 10% Ficoll, 5% SDS, 0.2% bromphenol blue) containing proteinase K (1.0 mg/ml) for 2 hours at room temperature. Incorporated radioactivity was analyzed by electrophoresis on a 0.8% agarose gel (50V, 20 hours) followed by vacuum drying the gel and counting on a Betascope.

As indicated by Table 2, the addition of 10 µM cAMP inhibits DNA replication in activated nuclei as compared to DNA replication occurring without any cAMP. DNA replication increased with 0.1 µM and 1.0 µM cAMP. A greater increase was seen with 1.0 µM than with 0.1 µM cAMP. Thus, cAMP can be used to increase the activation activity of activating egg extracts. A concentration of approximately 0.3 µM, was used in subsequent studies.

TABLE 2

| Cpm Incorporated After X Minutes | Micromoles of Cyclic AMP Added | | | |
|---|---|---|---|---|
| | 0.0 | 0.1 | 1.0 | 10 |
| 0 | 14 | 14 | 10 | 43 |
| 45 | 37 | 51 | 14 | 34 |
| 90 | 73 | 68 | 56 | 31 |
| 135 | 288 | 290 | 564 | 35 |
| 180 | 839 | 1,141 | 2,316 | 85 |
| 240 | 1,556 | 2,945 | 4,484 | 168 |
| 300 | 2,954 | 2,692 | 5,504 | 571 |

Example 2

Caffeine Supplemented Activating Egg Extract

The effect of caffeine on DNA replication in activated Xenopus red blood cells was determined. The experimental conditions used were as described in Example 1 with the following changes: the concentration of cAMP was set at 0.3 µM and caffeine was added to the activating egg extract to a concentration of either 0.2 mM, 1.0 mM, or 5.0 mM.

Figure 1:
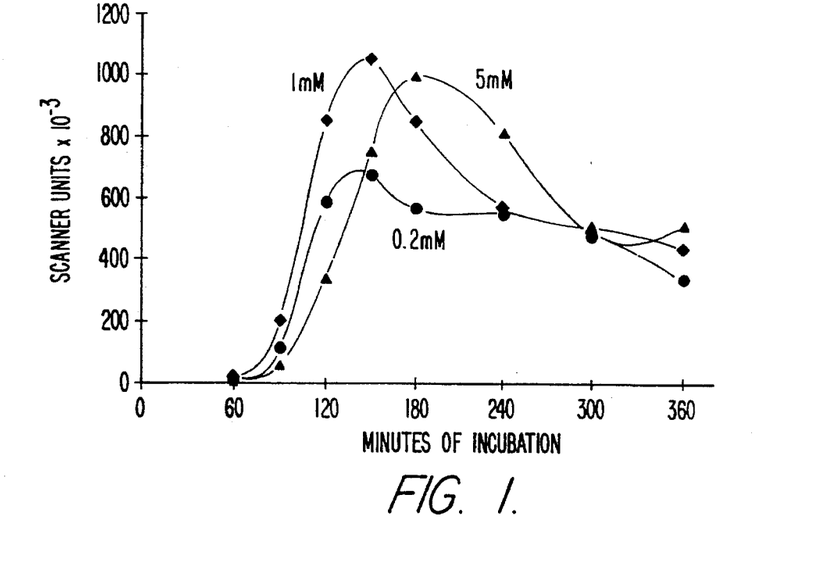
FIG. 1 shows the effect on DNA replication of activated nuclei, of using frozen/thawed activating egg extracts supplemented with caffeine.

As illustrated by FIG. 1, caffeine at 1.0 mM in the presence of 0.3 µM cAMP gave the highest initial rate and extent of DNA replication in activated nuclei. Thus, caffeine can increase the activation activity of an activating egg extract.

Example 3

CSF Extract Supplemented with DMAP

Addition of 6-dimethylamino purine (DMAP) to CSF extracts was used to further pretreat Xenopus erythrocyte nuclei and stimulate subsequent DNA replication in activating egg extract. Xenopus erythrocyte nuclei were isolated and pretreated as described in Example 1 above, and incubated in thawed "prepared CSF extract" supplemented with 80 mM β-glycerol-PO$_4$, and 5 µg/ml nocodazole at a concentration of 2000 nuclei/µml. Further pretreatment was carried out by incubation for 30 minutes at 4° C. then 30 minutes at 25° C., then 60 minutes at 4° C. Half the samples were supplemented with 5 mM DMAP before addition of the nuclei. After the two hours of incubation, each sample was diluted with 9 volumes of activating egg extract, supplemented with 5 µg/ml nocodazole (this dose of nocodazole slows down the rate of replication) and approximately 160 µCi/ml P$^{32}$-dCTP. Aliquots were removed over time to measure DNA replication.

Figure 2:
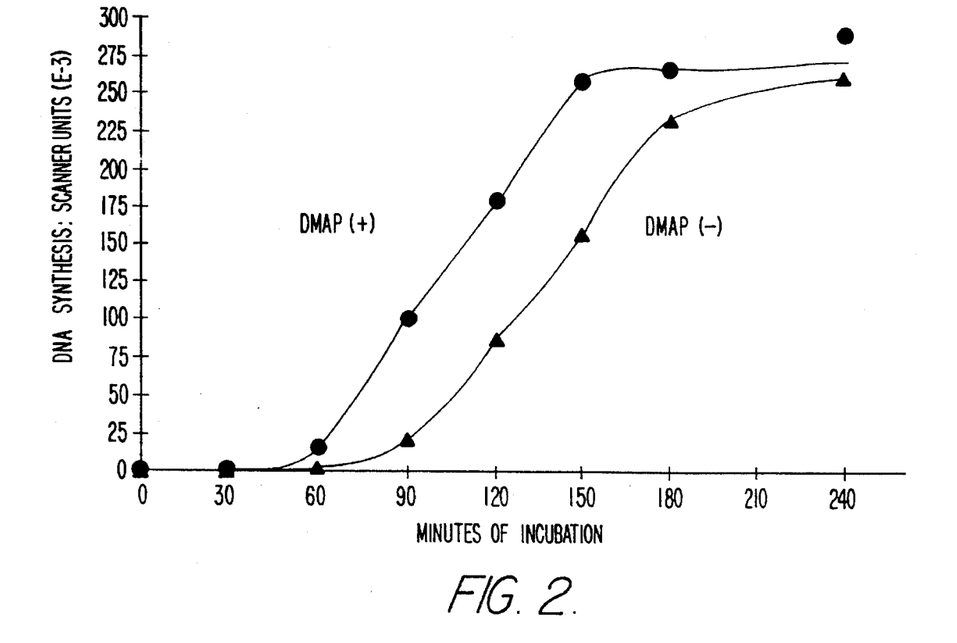
FIG. 2 shows the effect on DNA replication of activated nuclei, of using CSF extract supplemented with 6-dimethylamino-purine (DMAP).

As illustrated by FIG. 2, the addition of DMAP to CSF extracts enhanced the ability of the CSF extract to stimulate subsequent DNA replication in activating egg extract. DMAP decreased the lag time before the onset of replication and increased the initial rate and total amount of DNA synthesis.

Example 4

Warm-Then-Cold Regime

Various warm-then-cold regimes used as part of a further pretreatment increased DNA replication in activated nuclei. Thawed Xenopus erythrocyte nuclei (isolated and pretreated as in Example 1 above) were added at 2000 nuclei/µl to thawed "prepared CSF extract," supplemented with 80 mM β-glycerol-PO$_4$. The mixture was incubated using various warm-then-cold regimes. At the end of each incubation period samples was diluted with 9 volumes of "prepared activating egg extract" supplemented with 5 µg/ml nocodazole and P$^{32}$-dCTP. Samples were removed over time to measure the extent of DNA replication.

Figure 3:
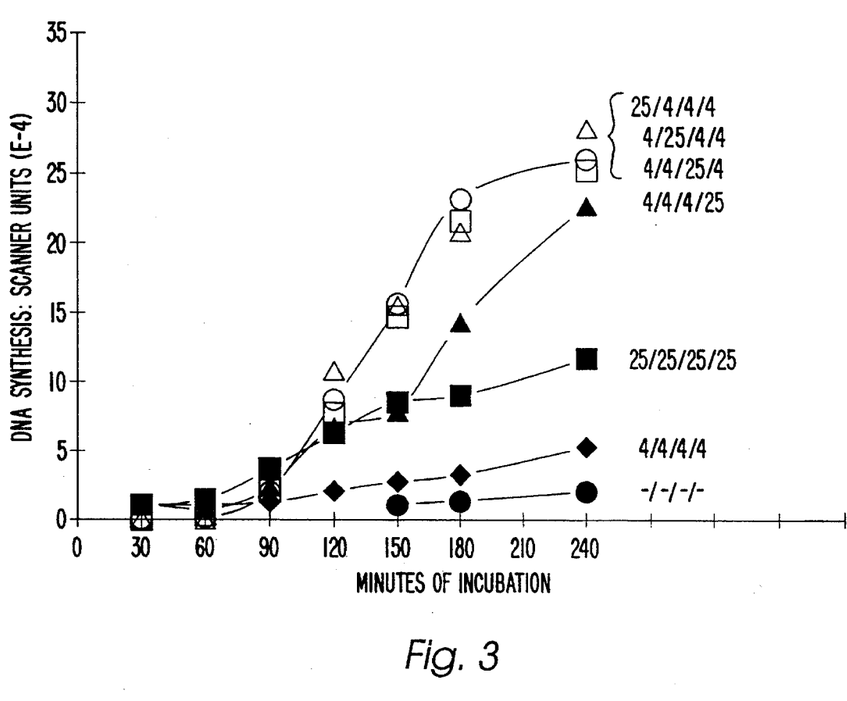
FIG. 3 shows the effect of various warm-then-cold protocols on DNA replication in activated nuclei.

As shown by the data represented in FIG. 3, the following warm-then-cold regimes stimulated subsequent DNA replication: 30 minutes at 25° C., and 90 minutes at 4° C. ; 30 minutes at 4° C., 30 minutes at 25° C., and 60 minutes at 4° C.; 60 minutes at 4° C., 30 minutes at 25° C., and 30 minutes at 4° C. Incubation for 90 minutes at 4° C., and 30 minutes at 25° C. was not as effective as incubation regimes that had a warm period followed by a cold period. Thus, nuclei activation is preferably performed using a warm-then-cold regime.

Example 5

Activation Using Frozen/Thawed Extracts

Activation of Xenopus red blood cell nuclei was studied using frozen/thawed CSF extracts and frozen/thawed activating egg extract. Xenopus red blood cell nuclei were isolated and pretreated as described in example 1. These nuclei were further pretreated at 2000 nuclei/µl in thawed "prepared CSF extract" supplemented with 10 mM creatine phosphate, 10 µg/ml creatine phosphokinase, 5 µg/ml nocodazole, 80 mM β-glycerol-PO$_4$, 100 µM CaCl$_2$ and incubated using a warm-then-cold format of 60 minutes at 25° C. followed by 60 minutes at 4° C.

After further pretreatment, samples were diluted with 9 volumes of thawed "prepared activating egg extract" containing 10 mM creatine phosphate, 10 µg/ml creatine phosphokinase, and incubated with either: A) 200 µCi/ml p$^{32}$-dCTP; B) 16 µM biotin-11-dUTP, 16 µM MgCl$_2$; or C) no additions.

At various time intervals an aliquot of each incubation was treated as follows:

A) P$^{32}$-labelled samples were treated with sodium dodecyl sulfate (SDS), proteinase-K, and then analyzed on agarose gels to determine DNA replication. Total incorporated radioactivity was measured using a Molecular Dynamics phosphoimager. The sizes of the radioactive molecules were observed and photographed on X-ray film.

B) Biotin labelled nucleic acid was used to visualize replicated nuclear DNA. Biotin labelled samples were fixed by mixing into approximately 40 volumes of freshly prepared 1.0 mM ethylene glycol bis-(succinic acid N-hydroxysuccinimide ester) (EGS) and incubated at 37° C. for 30 minutes. Fixed nuclei were stored at 8° C. for 48 hours and then centrifuged onto glass Coverslips (2000 rpm, at 4° C. for 15 minutes) through a 25% glycerol layer. The glycerol layer was removed and the samples were stained with Texas Red-Streptavidin (Gibco BRL, diluted 1:40 in PBS). Coverslips were then washed with buffered saline and stained with 1.0 µg/ml Hoechst 33258 stain (for total DNA). Each sample was examined and photographed at 60× using an Olympus optical system. Using these conditions: 1) nuclear envelopes were detected under phase optics as a dark line around the nucleus; 2) total nuclear DNA was observed under fluorescent optics as Hoechst positive (blue) staining; 3) newly replicated biotinylated DNA were detected as Texas Red positive (red) staining.

C) Samples from incubate (C) were used to measure histone H1 kinase activity during the course of the experiment.

As judged by both $P^{32}$-dCTP incorporation and biotinylated-dUTP incorporation, new DNA replication in erythrocyte nuclei was highly synchronous and efficient. Replication began at 30–40 minutes of incubation and was completed by 80–90 minutes of incubation. No additional DNA synthesis was observed between 90–140 minutes. After 140 minutes DNA replication resumed. The initial rate of DNA synthesis in this system using frozen/thawed activating egg extract is only slightly slower than that using fresh activating egg extract. Furthermore, it appears that replication of the entire genome is achieved.

As judged by nuclear morphology and staining, swelling was observed about 20 minutes after addition of activating egg extract (T=20). At T=20 no DNA replication was observed. DNA synthesis and biotinylated-dUTP incorporation were both first observed at T=40. Nuclear swelling continued until T=80 at which time nuclear condensation and nuclear envelope breakdown began. Photographs of 10 or more nuclei at each time point revealed that virtually all nuclei in each sample were activated at the same time and in the same manner. Hoechst staining and biotin labelling revealed that nuclear DNA was first highly compacted (T=0), became more diffuse during the period of swelling and replication (T=20 to T=80), and then condensed into chromosome like structures (T=100 to T=180). Nuclear envelope breakdown occurred at T=100 to T=120 minutes, but mitotic spindle formation was not observed in these samples. This is likely due to the presence of low levels of nocodazole (0.5 µg/ml). At T=160 many of the nuclei appeared under phase contrast to have nuclear envelopes suggesting they entered a second interphase. All nuclei at T=180 had distinct chromosome-like structures indicating that they entered a second mitosis. DNA synthesis ($P^{32}$-dCTP incorporation) resumed between T=140 and T=160 and then stopped at T=160 in accord with a second S-phase followed by a second mitosis.

Histone H1 kinase levels were low at the start of S-phase (T=40) and rose gradually thereafter. Correlations of DNA synthesis, nuclear morphology, and H1 kinase levels suggested that a threshold level of H1 kinase leading to nuclear envelope breakdown and first mitosis was reached at T=100. H1 kinase levels continued to rise until T=180, despite the fact that DNA synthesis resumed at T=140–160.

First mitosis occurred relatively early (T=100 to T=120) and was not accompanied by DNA fragmentation. These observations are consistent with the view that genome replication was complete in this experiment. Agarose gel analysis of the $P^{32}$-labelled DNA demonstrated that virtually all newly synthesized DNA was initially of very high molecular weight (HMW), some of this material was then converted to pieces of a rather uniform moderate molecular weight (MMW). DNA pieces of the MMW size are not degradation products and reflect a fundamental unit of DNA packaging in condensing chromosomes. MMW may be due to experimental interruption of topoisomerase II dependent deconcatenation of replicated DNA loops.

In summary this experiment demonstrates, an in vitro system using frozen/thawed CSF extracts, and frozen/thawed activating egg extracts prepared from Xenopus eggs. In this system nuclei swell, acquire new envelopes, and cycle through at least one complete S phase followed by one complete M phase. Only a limited amount of DNA synthesis takes place in a second S-phase. This system permits highly synchronous activation and cycling of quiescent cell nuclei, and is directly applicable to the activation of human fetal erythrocytes, amniotic fluid cells, and sperm nuclei.

Example 6

Microchamber Microscope Slide

The use of the microchamber microscope slide to analyze and activate nuclei is shown below. Xenopus erythrocyte nuclei were isolated and pretreated as described above in Example 1. These nuclei, in NIB buffer, were allowed to settle onto the lower surface of several microchamber microscope slides. A coverslip was placed over each sample and sealed using oil along the sides. Nuclei were further pretreated using thawed "prepared CSF extract" made 80 mM in β-glycerol-$PO_4$ and supplemented with 10 mM creatine phosphate and 10 µg/ml creatine phosphokinase. Ten microliters of CSF extract was allowed to flow into each well and the microchamber microscope slide was then subjected to the following warm-then-cold treatment; 30 minutes on ice, 30 minutes at 25° C., and 30 minutes on ice. After the warm-then-cold treatment, the CSF extract in each well was displaced by the addition of 20 µl freshly "prepared activating egg extract" containing biotinylated-dUTP. The microchamber microscope slides were then warmed to 25° C. At varying lengths of time the incubations were stopped by rinsing the microchamber with 75 µl of an appropriate buffer containing Texas red streptavidin (for detection of incorporated biotin), followed by staining with Hoechst stain for detection of total DNA. The nuclei were photographed at a magnification of 60× using fluorescent optics.

Red blood cell nuclei before pretreatment were small and compact. The majority of nuclei were separated from one another indicating they were not damaged or clumped during isolation.

Red blood cell nuclei at the end of further pretreatment in CSF extract were attached to the surface of the microchamber microscope slide and remained small and highly compact.

Red blood cell nuclei 30 minutes after addition of activating egg extract swelled dramatically, and were attached to the surface of the slide. Texas red streptavidin staining of these nuclei demonstrated the lack of DNA replication.

Nuclei after 85 minutes of incubation in activating egg extract were swollen. As seen by Texas red streptavidin staining, these nuclei were surrounded with a nuclear envelope and initiated DNA replication.

After 150 minutes of incubation in fresh activating egg extract DNA replication was complete and the nuclei entered mitosis. As a result of entering mitosis, the nuclear envelopes dissembled and the DNA condensed into chromosome-like structures which remained attached to the surface of the microchamber microscope slide.

These results demonstrate the utility of a microchamber microscope slide in nuclei activation. Using the methods and products disclosed in the present invention nuclei were conveniently activated on a microchamber microscope slide.

Example 7

Activation of Human Fetal Red Blood Cell

The activation of human fetal red blood cells using activating egg extract is described below. Human fetal red blood cells were prepared from umbilical cord blood, pretreated with lysolecithin and trypsin, and contacted with activating egg extract.

Human fetal red blood cells were isolated from umbilical cord blood and fractionated into a nucleated cell fraction and a non-nucleated cell fraction as described by Bianchi et al., *Proc. Natl. Acad. Sci. U.S.A.* 87:3279 (1990). Accordingly, a sample of neonatal umbilical cord blood was drawn into a vacuum tube containing anticoagulants, the blood was diluted 1:1 with Hank's balanced salt solution (HBSS) (Hanks and Wallace, *Proc. Exp. Biol. Med.* 71:196 (1949)), layered over a Ficoll/Hypaque column (Pharmacia) and spun at 1400 rpm for 40 min at room temperature. The mononuclear cell layer was recovered and washed twice by centrifugation in HBSS. The cells were then washed several times in NIB buffer (250 mM sucrose, 25 mM NaCl, 10 mM Pipes, 1.5 mM $MgCl_2$, 0.5 mM spermidine, 0.15 mM spermine, pH 7.0); the resulting cell pellet was suspended in NIB:Glycerol (7:3) and frozen in liquid nitrogen as 100µl aliquots containing $6.3 \times 10^6$ cells.

Frozen cells were thawed at room temperature and put on ice, washed twice with NIB, diluted to $4 \times 10^7$ cells/ml in NIB at 23° C., and added to an equal volume of NIB containing 80 µg/ml lysolecithin and 0.6 µg/ml trypsin; lysolecithin and trypsin treatment was halted after 5 minutes by adding soybean trypsin inhibitor to a concentration of 10 µg/µl and bovine serum albumin to a final concentration of 0.4%. Isolated nuclei were added directly to thawed "prepared activating egg extract" to a concentration of 200 nuclei/µl, supplemented with 10 mM creatine phosphate, 10 µg/ml creatine phosphokinase, 5 µg/ml nocodazole, 0.3 mM cAMP, and 1 mM caffeine. One aliquot of this sample was supplemented with $P^{32}$-dCTP at approximately 200 µCi/ml and used to measure DNA replication. A second aliquot was sampled periodically for fluorescent microscopic examination of nuclei after fixation and staining with Hoechst dye (as described above).

Human red blood cell nuclei treated in the manner described above swelled significantly during the first 90 minutes and initiated DNA synthesis. DNA synthesis continued for approximately 4.0 hours after which nuclear chromatin condensed. However, the observed kinetics of DNA synthesis indicated that complete genome replication was not achieved in this experiment. The failure to achieve complete genome replication was probably due to the failure to further pretreat the isolated human nuclei in CSF extract and because activating egg extract contained a relatively high level of nocodazole, ie. 5 µg/ml.

Despite the difficulties encountered, the formation of metaphase chromosomes demonstrates that the present invention can be used to activate non-dividing human nuclei. The non-dividing human nuclei activated analogously to Xenopus erythrocyte nuclei. Therefore, the various improvements described in the present invention, such as further pretreatment in CSF extract, a warm-then-cold regime and the addition of 100 µM $CaCl_2$, which result in increasing the activation of non-dividing Xenopus erythrocyte are applicable to activate non-dividing human nuclei.

Other embodiments are within the following claims.

I claim:

1. A method for in vitro activation of a nucleus from a human fetal red blood cell or a fetal cell found in amniotic fluid comprising the steps of:

a) separating said nucleus from said human fetal red blood cell or said fetal cell from its surrounding cytoskeleton using a protease and a non-ionic detergent to form a pretreated nucleus, b) contacting said pretreated nucleus with cytostatic factor extract, and c) contacting said pretreated nucleus from said step b with an activating egg extract to activate said pretreated nucleus.

2. The method of claim 1, where said protease is trypsin and said detergent is lysolecithin.

3. The method of claim 1, wherein said nucleus is activated under conditions were the nucleus and its chromosomes does not divide.

4. The method of claim 3, wherein said conditions comprise adding nocodazole to said activating egg extract or said cytostatic factor extract.

5. The method of claim 4, wherein said nocodazole is in amount less than 5 µg/ml.

* * * * *

UNITED STATES PATENT AND TRADEMARK OFFICE
CERTIFICATE OF CORRECTION

PATENT NO. : 5,480,772
DATED : January 2, 1996
INVENTOR(S) : Wangh, Lawrence J.

It is certified that error appears in the above-indentified patent and that said Letters Patent is hereby corrected as shown below:

Col. 7, Line 1, There should be a period at the end of the sentence.

Col. 17, Line 8, change "HI" to --H1--.

Col. 24, Line 18, change "CAMP" to --cAMP--.

Col. 25, Line 52, change "nuclei/$\mu$ml" to --nuclei/$\mu$l--.

Signed and Sealed this

Twenty-sixth Day of November 1996

Attest:

BRUCE LEHMAN

Attesting Officer

Commissioner of Patents and Trademarks